United States Patent [19]
Hardtmann

[11] 4,160,032
[45] Jul. 3, 1979

[54] OXINDOLES AS SLEEP-INDUCERS

[75] Inventor: Goetz E. Hardtmann, Florham Park, N.J.

[73] Assignee: Sandoz, Inc., E. Hanover, N.J.

[21] Appl. No.: 525,005

[22] Filed: Nov. 18, 1974

Related U.S. Application Data

[63] Continuation-in-part of Ser. No. 417,815, Nov. 21, 1973, abandoned, which is a continuation-in-part of Ser. No. 338,997, Mar. 7, 1973, abandoned.

[51] Int. Cl.² .............................................. A61K 31/40
[52] U.S. Cl. ..................................................... 424/274
[58] Field of Search ......................................... 424/274

[56] References Cited
PUBLICATIONS

Muller et al., Med. Exp. 11 (3), pp. 149–156, (1964).

Orcutt et al., Arch. Int. Paracodyn 152, pp. 121–131, (1964).

Primary Examiner—Jerome D. Goldberg
Attorney, Agent, or Firm—Gerald D. Sharkin; Richard E. Vila

[57] ABSTRACT

Sleep inducers of the formula:

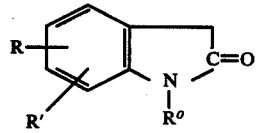

wherein R is hydrogen or halo of atomic weight of from 18 to 36, R' is hydrogen, halo or $CF_3$ and R° is hydrogen or lower alkyl. Preparation by cyclizing a 2-nitrophenylacetic acid is also disclosed.

17 Claims, No Drawings

OXINDOLES AS SLEEP-INDUCERS

This application is a continuation-in-part of application Ser. No. 417,815, filed Nov. 21, 1973, now abandoned which is a continuation-in-part of application Ser. No. 338,997, filed Mar. 7, 1973, now abandoned.

This invention relates to chemical compounds which are oxindoles, to their preparation and to the utilization of said compounds based on their pharmacological activity.

Oxindole itself and certain substituted and/or N-alkyl substituted oxindoles have been disclosed in the literature. For example, 5-chloro-oxindole is known and commercially available and 4-chloro-oxindole is also known. In addition, many N-alkyl substituted oxindoles including those which are also halo substituted have been described as chemical intermediates by E. H. Wiseman et al., J. Med. Chem. 16, (2), 131–133(1973). To my knowledge none of the above-referred to halo-substituted oxindoles has been associated with pharmaceutical activity. On the other hand, oxindole itself and certain N-alkyl oxindoles have been disclosed as possessing CNS depressant activity in mice and other animals. For example, M. Muller et al., Med. Exp. 11, (3), 149 (1964) indicate that oxindole has anticonvulsant activity and potentiates hexobarbital anesthesia at moderate doses while causing an anesthetic type effect just prior to death at higher doses. Oxindole, N-methyl oxindole and N-ethyl oxindole are also disclosed as having CNS depressant and anti-convulsant activities by J. A. Orcutt et al., Arch. Int. Paracodyn. 152, 121 (1964). Also, various alkoxy-substituted oxindoles were evaluated pharmacologically with apparently mixed results including an indication of sedative and analgetic activities, see J. Walker et al., J. Med. Chem., 13, (65), 983–985 (1970) and the references cited therein, including French Medicament Pat. No. 1657M.

In accordance with the present invention, it has been found that sleep may be induced in animals by administering a compound of the following formula I:

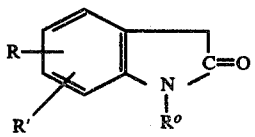

wherein
R is hydrogen or halo of atomic weight of from 18 to 36, i.e., fluoro or chloro,
R' is hydrogen, halo of atomic weight of from 18 to 36 or trifluoromethyl, and
R° is hydrogen or lower alkyl of 1 to 4 carbon atoms.

The compounds of the formula I in which R° is hydrogen may be prepared by known procedures for the preparation of oxindoles. A preferred procedure which I have developed involves the preparation of compounds of the formula I by subjecting a compound of the formula II:

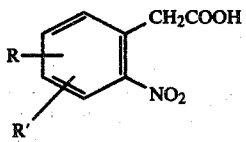

wherein R and R' are as defined to reductive cyclization.

The preparation of compounds I by reductive cyclization of a compound II is carried out in a liquid solvent medium and may be effected by subjecting a compound II to reduction in a known manner for reducing an aromatic nitro substituent to the primary amino group. Such reduction may be carried out, for example, by using conventional reducing agents, e.g., stannous chloride, zinc and the like or by catalytic hydrogenation techniques employing, for example, Raney Nickel, palladium and the like. The preferred solvents for the reaction are dependent upon the type of reduction employed, for example, the lower alcohols and cyclic and acyclic ethers with reducing agents such as stannous chloride, acetic acid when employing zinc, and acetic acid and ethyl acetate when employing catalytic hydrogenation. The reduction may be carried out at temperatures in the range of from minus 20° C. to plus 100° C., preferably plus 10° C. to plus 40° C. It is postulated that the resulting amine cyclizes with the carboxy function of the compound II at the same temperature to yield the product of the formula I. The reaction mixture is preferably neutral or acidic during the reaction. The product of the formula I may be recovered by working up by established procedures.

The compounds of the formula II are either known or may be prepared from known materials by established procedures. For example, one method of preparation of said compounds II involves subjecting a compound of the formula III:

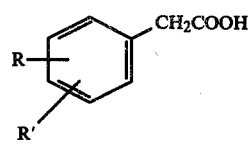

wherein R and R' are as defined, to aromatic nitration in a known manner, for example, by reaction with nitric and sulfuric acids at controlled temperatures, e.g., 0° C. to 40° C.

Another process for preparation of compounds II involves reacting a compound of the formula IV

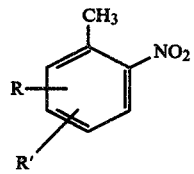

wherein R and R' are as defined, with diethyloxalate in the presence of a strong base, e.g., potassium tert. butoxide or sodium ethoxide, to obtain a compound of the formula V:

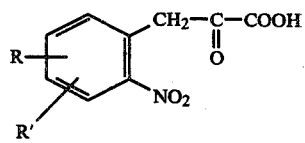

wherein R and R' are as defined, said compound 5 then being oxidized to obtain the compound of the formula II.

The preparation of the compounds V from compounds IV and the preparation of compounds II from compounds V as above indicated represent the application of known process technolodgy. Such preparation of compounds V may thus be carried out in an alcoholic solution, e.g., ethanol, at temperatures of from 50° C. to 120° C. followed by hydrolysis carried out at elevated temperatures, e.g., 80° C. to 120° C. compounds II are preferably prepared from compounds V employing hydrogen peroxide as the oxidizing agent in an alkaline aqueous solution at temperatures of typically 20° C. to 60° C. The employment of alternate procedures such as the preparation of compounds II via compounds IV and V may be preferred over the preparation of compounds II via compounds III in situations where the nitration of a compound III does not yield satisfactory quantities of product having the nitro group introduced at the desired ortho position relative to the carboxymethyl function.

The compounds of the formula III and IV are either known or may be prepared from known materials by established procedures.

The compounds of the formula I in which R° is alkyl may be prepared by cyclizing a compound of the formula VI

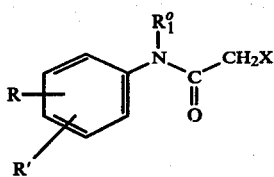

VI wherein R and R' are as defined, $R_1°$ is alkyl of 1 to 4 carbon atoms and X is bromo or chloro, preferably bromo.

The cyclization of a compound VI to produce the compounds I in which R° is alkyl is suitably effected by reacting a compound VI with a Friedel-Crafts reagent at elevated temperatures typically in the range of from 100° C. to 250° C., preferably 180° C. to 220° C. The reaction may be conveniently carried out in absence of a solvent but conventional inert organic solvents such as dichlorobenzene may be employed.

The compounds of the formula I in which R° is alkyl may be also prepared by reacting a compound of the formula IA:

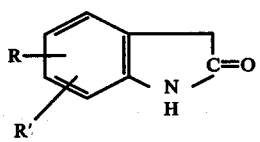

IA in which R and R' are as defined with a compound of the formula VII:

$X'R_1°$

VII in which X' is chloro, bromo or iodo, preferably iodo, and $R_1°$ is alkyl of 1 to 4 carbon atoms.

The preparation of compound I in which R° is alkyl from compound IA is suitably carried out at temperatures in the range of from 20° C. to 150° C., preferably 60° C. to 130° C., in the presence of an inert solvent and strong base such as an alkali metal hydride, e.g., sodium hydride, or an alkali metal alkoxide, e.g., sodium t-butoxide. Inert solvents are of conventional type, e.g., dimethylacetamide is preferably used when employing sodium hydride as the base and t-butanol is preferably used when t-butoxide is employed as the base. As is well known, the reaction may be carried out by first reacting the base with the compound IA in the solvent followed by reaction of the resulting metallo derivative of the compound IA with the compound of the formula VII.

The compound of the formulae VI and VII are either known or may be prepared from known materials by established procedures.

The compounds of the formula I are useful because they possess pharmacological activity in animals. In particular, the compounds exhibit a depressant effect on the Central Nervous System as determined by inhibiting N-sulfamoylazepine induced seizures in mice on administration (10–125 mg./kg. i.p.), by reinducing hexobarbital anesthesia in mice (10–125 mg./kg. i.v.) and by inducing sleep in sleep studies in the monkey (10–125 mg./kg. p.o.) in which the various stages of sleep are monitored by chronically implanted electrodes and the results compared with controls. The compounds of the formula I are therefore indicated for use as sleep inducers. Doses for such use of the compounds I will, of course, vary depending upon known factors. However, in general, satisfactory results in the use of the compounds of the formula I as sleep-inducers may be obtained on administration at a dose of from 1 to 150 milligrams per kilogram of body weight. For most larger mammals the administration of a single dose of from 80 to 2000 milligrams of a compound of the formula I at bedtime provides satisfactory results, desirably administered in admixture with a solid or liquid pharmaceutical carrier or diluent. Divided dosage forms may contain 40 to 1000 milligrams in admixture with such a carrier or diluent.

For the above use, the pharmaceutically useful compounds provided by the invention may be formulated in a conventional manner to contain an effective dose of one or more of said compounds as active ingredient together with one or more conventional ingredients including an inert pharmaceutically acceptable carrier adapted to provide a composition suitable for either oral administration or for administration parenterally in the form of an injectable solution or suspension. In general, the preferred compositions are those adapted for oral administration and conventional forms for this purpose are suitable, such as tablets, dispersible powders, granules, capsules, syrups, elixirs and the like. Such compositions for oral administration may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained reaction over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of administration are solid compositions, particularly hard-filled capsules and tablets.

A representative formulation for oral administration at bedtime to induce sleep is a tablet prepared by conventional tabletting techniques and containing the following ingredients:

| Ingredient | Weight (mg.) |
| --- | --- |
| 5-fluoro-1-methyl-oxindole | 200 |
| Tragacanth | 10 |
| Lactose | 147.5 |
| Corn Starch | 25 |
| Talcum | 15 |
| Magnesium Stearate | 2.5 |

Preferred compounds include those in which R is hydrogen or fluoro and R' is hydrogen or fluoro, particularly with R being hydrogen or 5-fluoro and/or R' being hydrogen or 6-fluoro, more preferably with R° being hydrogen or methyl, e.g., oxindole, 1-methyloxindole, 5-fluoro-oxindole and 5-fluoro-1-methyloxindole.

The following examples given for purposes of illustration only show representative compounds of this invention and the manner in which such compounds are prepared.

EXAMPLE 1

5-Fluoro-oxindole

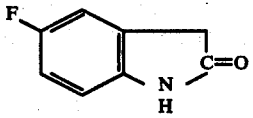

STEP A 5-fluoro-2-nitro-phenylacetic acid

To a mixture of 23.2 g. of 3-fluorophenylacetic acid and 100 ml. of conc. sulfuric acid is added dropwise 6.5 ml. of conc. nitric acid while maintaining the temperature below 40° C. The mixture is stirred at ambient temperature for 24 hours and then poured onto one kilogram of ice. The resulting precipitate is recovered by filtering, washed with water and dried in vacuo to obtain crude 5-fluoro-2-nitrophenylacetic acid, m.p. 137°–142° C.

STEP B 5-fluoro-oxindole

A mixture of 24 g. of 5-fluoro-2-nitro-phenylacetic acid, 2.0 g. of platinum oxide (PtO₂) and 250 ml. of glacial acid is hydrogenated at room temperature and 50 p.s.i. until the theoretical amount of hydrogen is taken up. The resulting mixture is filtered and the solvent evaporated off in vacuo. The residue is triturated with water and the resulting precipitate recrystallized from methylene chloride/diethyl ether to obtain 5-fluoro-oxindole, m.p. 131°–133° C.

EXAMPLE 2

6-Chloro-oxindole

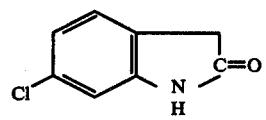

STEP A 3-(2-nitro-4-chlorophenyl)pyruvic acid

To a cooled mixture prepared by adding 13.6 g. of sodium to 300 ml. of ethanol is added a solution of 100 g. of 4-chloro-2-nitrotoluene and 84 g. of diethyloxalate in 150 ml. of ethanol while maintaining the temperature below 20° C. The resulting mixture is refluxed for one hour, cooled, 400 ml. of water added and the resulting mixture refluxed for 90 minutes. The ethanol is then evaporated to a small volume and the resulting precipitate contains tan and black material and the black material is mechanically separated and discarded and the remainder (filtrate plus tan precipitate) used in the next step.

STEP B 4-chloro-2-nitro-phenylacetic acid

The filtrate of Step A, above, is adjusted to pH 8–9 with 2 N sodium hydroxide and is heated at 35°–40° C. while adding a 3–6% aqueous hydrogen peroxide solution until samples no longer turn dark on treatment with 2 N sodium hydroxide. The tan precipitate is suspended in 1500 ml. of water, adjusted to pH 8–9 and similarly treated with aqueous hydrogen peroxide. The combined reaction mixtures are then acidified with concentrated hydrochloride acid to obtain a precipitate which are recovered by filtration, washed 3 times with water and dried in vacuo. The crude product (mp 145°–150° C.) is recrystallized from ether to obtain 4-chloro-2-nitro-phenylacetic acid, m.p. 156°–159° C.

STEP C

The product of Step B, above, is subjected to reductive cyclization analogously to Step B of Example 1 to obtain 6-chloro-oxindole, m.p. 185°–189° C.

EXAMPLE 3

Following the procedure of Example 1 there is also prepared:

(A) 5-chloro-oxindole, m.p. 197°–199° C.
(B) 6-fluoro-oxindole, m.p. 140°–142° C.
(C) 6-chloro-oxindole, m.p. 185°–189° C.
(D) 7-chloro-oxindole, m.p. 218°–220° C.
(E) 5,6-dichloro-oxindole, m.p. 209°–211° C.
(F) 5,6-difluoro-oxindole.
(G) 4-chloro-oxindole, m.p. 204°–207° C.
(H) oxindole.

EXAMPLE 4

5-Fluoro-1-methyloxindole

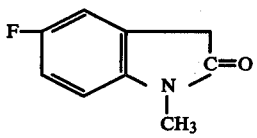

STEP A

Preparation of N-methyl-4-fluoro-α-bromoacetanilide

To a solution of 25.0 g. bromoacetyl bromide in 200 ml. of benzene is added dropwise 30.5 g. of N-methyl-4-fluoroaniline and the resulting solution is diluted with 70.0 ml. of benzene and then stirred for 18 hours at room temperature. The resulting precipitate is filtered off, and after washing down twice with benzene, the total filtrate is washed with 1 N hydrochloric acid and then with saturated sodium chloride solution, followed by drying, filtering and evaporation to obtain an oil which is distilled under vacuum (55°–65° C.) to obtain N-methyl-4-fluoro-α-bromoacetanilide.

STEP B

Preparation of 5-fluoro-1-methyloxindole

A mixture of 14.5 g. of N-methyl-4-fluoro-α-bromoacetanilide and 19.5 g. of aluminum trichloride is heated to 200° C. are maintained at 200° C. for 30 minutes. The resulting mixture while hot is poured into 300 g. of ice and the resulting precipitate is recovered by filtering, washed three times with water, dried and recrystallized from methylene chloride on adding diethyl ether to obtain 5-fluoro-1-methyloxindol, m.p. 128°–130° C.

EXAMPLE 5

Following the procedure of Example 4, the following compounds are prepared:
(A) 5-fluoro-1-ethyloxindole, m.p. 106°–109° C.
(B) 5-fluoro-1-n-propyloxindole.
(C) 6-fluoro-1-methyloxindole.
(D) 6-fluoro-1-ethyloxindole.
(E) 6-chloro-1-methyloxindole.
(F) 6-chloro-1-ethyloxindole.
(G) 5-chloro-1-methyloxindole.
(H) 5-chloro-1-ethyloxindole.
(I) 5,6-dichloro-1-methyloxindole.
(J) 5,6-difluoro-1-methyloxindole.
(K) 1-methyloxindole.
(L) 1-ethyloxindole.
(M) 5-trifluoromethyl-1-methyloxindole.

The compounds of the formula I may also be prepared by subjecting a compound of the formula VIII:

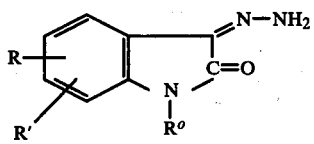

wherein R, R' and R° are as defined, to the action of a strong base at elevated temperatures.

The preparation of compounds I from compound VIII is suitably carried out at temperatures of from 20° C. to 120° C., preferably 50° C. to 100° C., and in an inert organic solvent. Suitable strong bases are the alkali metal alkoxides, e.g., sodium ethoxide, and the reaction using such alkoxides is conveniently effected in the corresponding alcohol as solvent.

The compounds of the formula VIII may be prepared by reacting a compound of the formula IX:

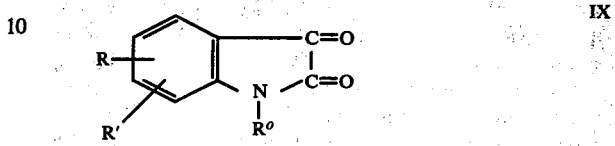

wherein R, R' and R° are as defined, with hydrazine in a known manner, preferably in an alcoholic solvent, e.g., ethanol, at temperature of from 30° C. to 100° C.

The compounds of the formula IX are either known or may be prepared from known materials by known procedures.

EXAMPLE 6

7-Chloro-oxindole

STEP A

Preparation of 7-chloro-3-hydrazono-oxindole.

A solution of 25.0 g. of 7-chloro-isatin in 250 ml. of ethanol is refluxed for 24 hours, cooled, and precipitate recovered by filtering and washed once with ethanol and twice with pentane to obtain 7-chloro-3-hydrazono-oxindole, m.p. 217°–219° C. (decomp.).

STEP B

Preparation of 7-chloro-oxindole.

To a solution of sodium ethoxide prepared by heating 5.5 g. of sodium in 200 ml. of ethanol at 70° C. is added 17 g. of 7-chloro-3-hydrazono-oxindole over a period of 3.5 hours, and the resulting solution is heated at 70° C. for 24 hours. The solvent is evaporated in vacuo, the residue dissolved in water, acidified with 6 N. hydrochloric acid and the resulting precipitate recovered by filtering, washed three times with water, dried by suction and crystallized from methylene chloride/ether to obtain 7-chlorooxindole, 218°–220° C.

The compounds of the formula I in which R° is hydrogen may also be prepared by subjecting a compound of the formula X:

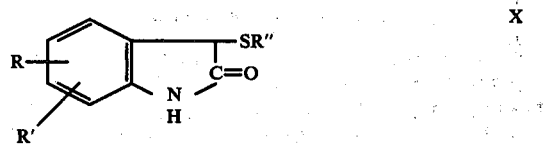

wherein R and R' are as defined and R'' is alkyl of 1 to 4 carbon atoms or phenyl, preferably alkyl, to desulfurization in the presence of a metal catalyst. The reaction is suitably carried out at temperatures of from 40° C. to 150° C., preferably 50° C. to 100° C. and in the presence of an inert organic solvent such as the lower alkanols, preferably methanol. Suitable metal catalyst include palladium on carbon in the presence of hydrogen and Raney Nickel. The reaction product of the formula I may be recovered from the reaction system in which it is formed by working up by conventional procedures.

The compounds of the formula X may be prepared by reacting a compound of the formula XI:

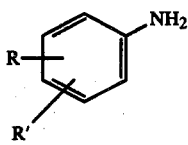

in which R and R' are as defined, with an organic hypochlorite and a compound of the formula XII:

wherein R" is as above defined and R'" is alkyl of 1 to 4 carbon atoms, preferably ethyl, in the presence of a base.

The preparation of compounds X as above indicated is generally carried out at temperatures in the range of from minus 80° C. to minus 20° C., preferably minus 70° C. to minus 40° C., and in the presence of an inert organic solvent such as methylene chloride. The reaction is desirably carried out in stages with the hypochlorite, e.g., t-butylhypochlorite, being first reacted with the aniline followed by addition of the compound of the formula XII and finally the base. Suitable bases include the tertiary amines such as triethylamine. The above described reaction is suitably followed up by the addition of a strong acid such as hydrochoric acid at temperatures of from minus 20° C. to plus 80° C., usually 0° C. to 40° C., and in general the reaction product of the formula X may be recovered by working up by established procedures.

EXAMPLE 7

5-Trifluoromethyl-oxindole

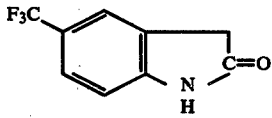

STEP A

Preparation of 5-trifluoromethyl-3-methylthio-oxindole

To a solution of 15.4 g. of p-trifluoromethylaniline in 400 ml. of methylene chloride cooled to minus 65° C. is added dropwise a solution of 10.2 g. of t-butyl hypochlorite in 20 ml. of methylene chloride. The solution is stirred at minus 65° C. for 5 minutes and there is then added dropwise 13.0 g. of thioacetic acid ethyl ester in 20 ml. of methylene chloride. The resulting mixture is stirred at minus 65° C. for 30 minutes. There is then slowly added 9.8 g. of triethylamine and the reaction mixture allowed to warm to room temperature at which time 200 ml. of 2 N. hydrochloric acid is added followed by stirring overnight at room temperature. There is then added 20 ml. of saturated sodium sulfite solution, the mixture stirred for 15 minutes, the aqueous phase separated and extracted into 1 N. sodium hydroxide solution and treated with 6 N. hydrochloric acid to obtain a precipitate. The precipitate is then extracted into methylene chloride, dried, filtered and the methylene chloride exchanged for ether and then pentane added to obtain 5-trifluoromethyl-3-methylthio-oxindole, m.p. 136°–138° C.

STEP B

Preparation of 5-trifluoromethyl-oxindole

A mixture of 4.0 g. of 5-trifluoromethyl-3-methylthio-oxindole, 20 g. of Raney Nickel and 100 ml. of methanol is refluxed for 4 days, cooled, treated with methylene chloride, filtered to remove the Raney Nickel and the filtrate concentrated in vacuo to obtain 5-trifluoromethyl-oxindole, m.p. 188°–190° C.

EXAMPLE 8

Following the procedure of Example 7, the following compounds are prepared.

(A) 4-trifluoromethyl-7-chloro-oxindole, m.p. 176°–179° C.
(B) 7-trifluoromethyl-oxindole, m.p. 204°–206° C.
(C) 7-fluoro-oxindole, m.p. 189°–192° C.

The compound 6-trifluoromethyl-oxindole has been previously disclosed in the literature as a chemical intermediate, see J. Or. Chem. Vol. 28, pgs. 3580–81 (1963).

What is claimed is:

1. The method of inducing sleep in an animal comprising administering to an animal in which said treatment is desired a sleep-inducing effective amount of a compound of the formula:

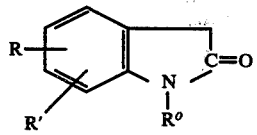

wherein
R is halo of atomic weight of from 18 to 36,
R' is hydrogen or halo of atomic weight of from 18 to 36, and
R° is hydrogen or alkyl of 1 to 4 carbon atoms.
2. The method of claim 1 in which the compound is 5-fluoro-oxindole.
3. The method of claim 1 in which the compound is 5-chloro-oxindole.
4. The method of claim 1 in which the compound is administered in a dose of from 80 to 2000 milligrams.
5. The method of claim 1 in which the compound is a compound in which R is 5-fluoro and R' is hydrogen.
6. The method of claim 5 in which the compound is a compound in which R° is hydrogen or methyl.
7. The method of claim 6 in which the compound is 5-fluoro-1-methyloxindole.
8. The method of claim 1 in which the compound is 7-chloro-oxindole.
9. The method of claim 1 in which the compound is a compound in which each of R and R' is fluoro.
10. The method of claim 9 in which the compound is a compound in which R is 5-fluoro and R' is 6-fluoro.
11. The method of claim 10 in which the compound is 5,6-difluoro-oxindole.
12. The method of claim 9 in which the compound is a compound in which R° is hydrogen.
13. The method of claim 9 in which the compound is a compound in which R° is alkyl of 1 to 4 carbon atoms.
14. The method of claim 13 in which the compound is a compound in which R° is methyl.
15. The method of claim 10 in which the compound is a compound in which R° is alkyl of 1 to 4 carbon atoms.

16. The method of claim 14 in which the compound is 5,6-difluoro-1-methyloxindole.
17. A pharmaceutical composition comprising from 80 to 2000 milligrams of a compound of the formula:
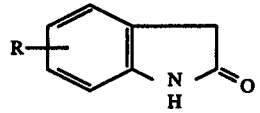
wherein R is fluoro or chloro, in association with a pharmaceutical carrier.